United States Patent [19]

Conrow et al.

[11] 4,130,660

[45] Dec. 19, 1978

[54] METHOD OF INHIBITING THE COMPLEMENT SYSTEM WITH TRISUBSTITUTED NAPHTHALENE COMPOUNDS

[75] Inventors: Ransom B. Conrow, Pearl River; Seymour Bernstein, New City, both of N.Y.

[73] Assignee: American Cyanamid Company, Stamford, Conn.

[21] Appl. No.: 846,489

[22] Filed: Oct. 28, 1977

Related U.S. Application Data

[62] Division of Ser. No. 782,212, Mar. 28, 1977, Pat. No. 4,087,613.

[51] Int. Cl.$^2$ .................... A61K 31/195; A61K 31/18

[52] U.S. Cl. ..................................... 424/319; 424/321
[58] Field of Search ................................ 424/321, 319

[56] References Cited

PUBLICATIONS

Chem. Abst., 9th col. Index, vol. 76–85, (1972–1976), p. 3222GS.

*Primary Examiner*—Sam Rosen
*Attorney, Agent, or Firm*—Claude J. Caroli

[57] ABSTRACT

1,3,5- or 1,3,6-naphthalenetriyltris(sulfonylimino)-aryl acids and salts, useful as complement inhibitors, and 1,3,5- or 1,3,6-naphthalenetriyltris(sulfonylimino)aryl acid esters which are intermediates, and the method for their preparation.

20 Claims, No Drawings

METHOD OF INHIBITING THE COMPLEMENT SYSTEM WITH TRISUBSTITUTED NAPHTHALENE COMPOUNDS

This is a division of application Ser. No. 782,212 filed Mar. 28, 1977 now U.S. Pat. No. 4,087,613.

DESCRIPTION OF THE INVENTION

The first embodiment of the invention is represented by a compound of the formula:

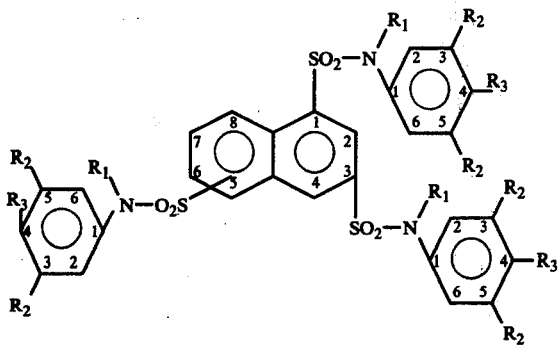

wherein $R_1$ is selected from the group consisting of hydrogen and methyl; $R_2$ is selected from the group consisting of hydrogen, carboxyl and $COOR_4$, wherein $R_4$ is selected from the group consisting of alkali metal and alkaline earth metal; $R_3$ is selected from the group consisting of hydrogen, hydroxy and $COOR_4$, wherein $R_4$ is as previously defined; with the proviso that each phenyl must contain at least one $COOR_4$; and the non-toxic pharmaceutically acceptable salts thereof.

A preferred embodiment of the first embodiment consists of those compounds wherein each phenyl is only mono-substituted from the group consisting of $COOR_4$, wherein $R_4$ is as previously defined.

A second preferred embodiment of the first embodiment consists of those compounds wherein each phenyl is only di-substituted from the group consisting of $COOR_4$, wherein $R_4$ is as previously defined.

A third preferred embodiment of the first embodiment consists of those compounds wherein each phenyl is only tri-substituted from the group consisting of $COOR_4$, wherein $R_4$ is as previously defined.

A most preferred embodiment of the first preferred embodiment consists of those compounds wherein each phenyl is only mono-substituted at the carbon 3-position or carbon 4-position and the floating phenyl is at the carbon 6-position on the naphthalene.

A most preferred embodiment of the second preferred embodiment consists of those compounds wherein each phenyl is only di-substituted at the carbon 3,5-position and the floating phenyl is at the carbon 6-position on the naphthalene.

A most preferred embodiment of the third preferred embodiment consists of those compounds wherein the floating phenyl is at the carbon 6-position on the naphthalene.

The second embodiment of the invention is represented by a compound of the formula:

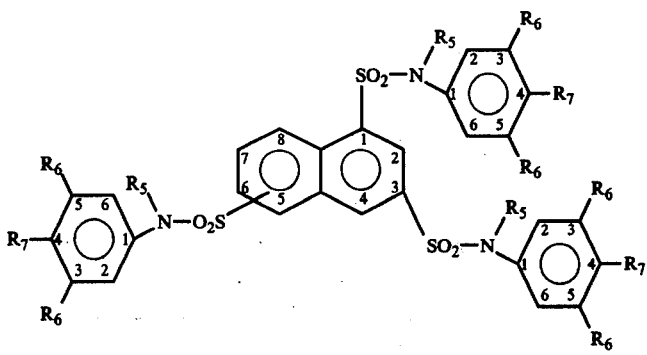

wherein $R_5$ is selected from the group consisting of hydrogen and methyl; $R_6$ is selected from the group consisting of hydrogen, methoxycarbonyl, 2-methoxyethoxycarbonyl and phenoxycarbonyl; and $R_7$ is selected from the group consisting of hydrogen, hydroxy, methoxycarbonyl and phenoxycarbonyl.

A preferred embodiment of the second embodiment consists of those compounds wherein each phenyl is only tri-substituted.

A most preferred embodiment of the preferred embodiment consists of those compounds wherein said phenyl is only tri-substituted with either 2-methoxyethoxycarbonyl or phenoxycarbonyl and the floating phenyl is at the carbon 6-position of the naphthalene.

The novel intermediates of this invention may be prepared as set forth immediately below. A compound of the formula:

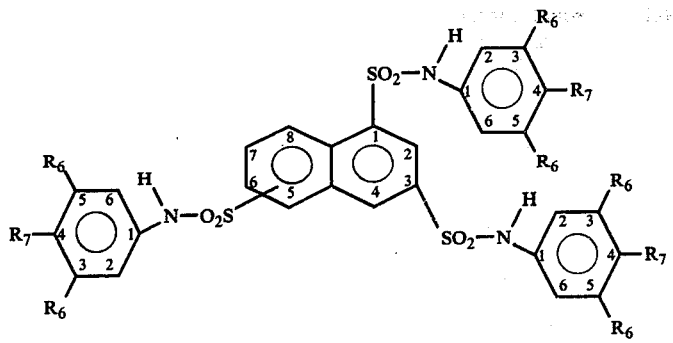

wherein $R_6$ is selected from the group consisting of hydrogen, methoxycarbonyl, 2-methoxyethoxycarbonyl and phenoxycarbonyl; and $R_7$ is selected from the group consisting of hydrogen, hydroxy, methoxycarbonyl and phenoxycarbonyl; is made by reacting a compound of the formula:

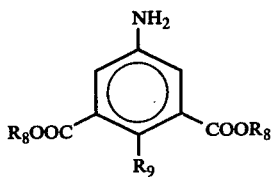

wherein $R_8$ is selected from the group consisting of $C_1$-$C_6$ alkyl; and $R_9$ is selected from the group consisting of hydrogen, hydroxy and $COOR_8$, wherein $R_8$ is as previously defined; with 1,3,6-naphthalenetrisulfonyl chloride in a suitable diluent with a suitable acid acceptor for about 40 minutes to about 18 hours. The suitable diluent is selected from the group of polar solvents such as pyridine, acetonitrile, triethylamine and the like. The suitable acid acceptor is selected from the group of organic and inorganic bases such as pyridine, triethylamine, sodium carbonate, sodium acetate, quinoline, calcium oxide, calcium hydroxide and aluminum hydroxide. The methylated form of the novel intermediates is obtained by reacting them with methyl iodide in the presence of a strong base such as sodium hydroxide.

The novel complement inhibiting compounds of this invention are as set forth immediately below. A compound of the formula:

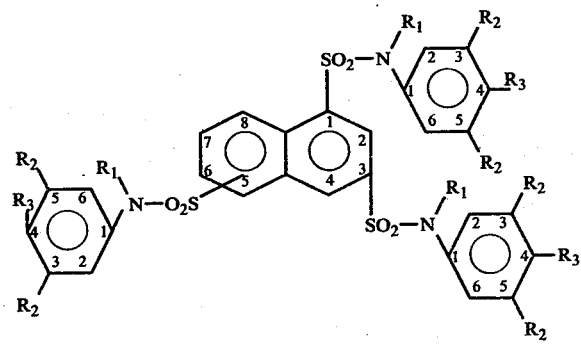

wherein $R_1$ is selected from the group consisting of hydrogen and methyl; $R_2$ is selected from the group consisting of hydrogen, carboxyl and $COOR_4$, wherein $R_4$ is selected from the group consisting of alkali metal and alkaline earth metal; $R_3$ is selected from the group consisting of hydrogen, hydroxy and $COOR_4$, wherein $R_4$ is as previously defined; with the proviso that each phenyl must contain at least one $COOR_4$; is made by reacting the appropriate novel intermediates, as shown and described above, in an alkali metal hydroxide for about 45 minutes to about 16 hours and then neutralizing with a suitable weak acid capable of removing the N-alkali salt of the sulfamido moiety. The alkali metal hydroxide may be sodium hydroxide or the like, and the weak acid may be a mineral acid or $C_1$-$C_4$ alkanoic acid.

The term "complement" refers to a complex group of proteins in body fluids that, working together with antibodies or other factors, play an important role as mediators of immune allergic, immunochemical and/or immunopathological reactions. The reactions in which complement participates take place in blood serum or in other body fluids, and hence are considered to be humoral reactions.

With regard to human blood, there are at present more than 11 proteins in the complement system. These complement proteins are designated by the letter C and by number: C1, C2, C3 and so on up to C9. The complement protein C1 is actually an assembly of subunits designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its role in body processes can be found in, for example, Bull. World Health Org., 39, 935–938 (1968); Ann. Rev. Medicine 19, 1–24 (1968); The John Hopkins Med. J., 128, 57–74 (1971); Harvey Lectures, 66, 75–104 (1972); The New England Journal of Medicine, 287, 452–454; 489–495; 545–549; 592–596; 642–646 (1972); Scientific American, 229, (No. 5), 54–66 (1973); Federation Proceedings, 32, 134–137 (1973); Medical World News, October 11, 1974, pp. 53–58; 64–66; J. Allergy Clin. Immunol., 53, 298–302 (1974); Cold Spring Harbor Conf. Cell Proliferation 2/Proteases Biol. Control/229–241 (1975); Annals of Internal Medicine, 84, 580–593 (1976); "Complement: Mechanisms and Functions", Prentice-Hall, Englewood Cliffs, N.J. (1976).

The complement system can be considered to consist of three sub-systems: (1) a recognition unit (C1q) which enables it to combine with antibody molecules that have detected a foreign invader; (2) an activation unit (C1r, C1s, C2, C4, C3) which prepares a site on the neighboring membrane; and (3) and attack unit (C5, C6, C7, C8 and C9) which creates a "hole" in the membrane. The membrane attack unit is non-specific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to the host's cells. Immunity is therefore a double-edge sword.

Activation of the complement system also accelerates blood clotting. This action comes about by way of the complement-mediated release of a clotting factor from platelets. The biologically active complement fragments and complexes can become involved in reactions that damage the host's cells, and these pathogenic reactions can result in the development of immune-complex diseases. For example, in some forms of nephritis, complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus, it is an autoimmune disease in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection it also results in inflammation and tissue damage in the immunopathological process. The nature of certain of the complement proteins, suggestions regarding the mode of complement binding to biological membranes and the manner in which complement effects membrane damage are discussed in Annual Review in Biochemistry, 38, 389 (1969).

A variety of substances have been disclosed as inhibiting the complement system, i.e., as complement inhibitors. For example, the compounds 3,3'-ureylenebis-[6-(2-amino-8-hydroxy-6-sulfo-1-naphthylazo)]benzenesulfonic acid, tetrasodium salt (chlorazol fast pink), heparin and a sulphated dextran have been reported to have an anticomplementary effect, British Journal of Experimental Pathology, 33, 327–339 (1952). The compound 8-(3-benzamido-4-methylbenzamido)naphthalene-1,3,5-trisulfonic acid (Suramin) is described as a competitive inhibitor of the complement system, Clin. Exp. Immunol., 10, 127–138 (1972). German Pat. No. 2,254,893 or South African Pat. No. 727,923 discloses certain 1-(diphenylmethyl)-4-(3-phenylallyl)piperazines useful as complement inhibitors. Other chemical compounds having complement inhibiting activity are disclosed in, for example, Journal of Medicinal Chemistry, 12, 415–419; 902–905; 1049–1052; 1053–1056 (1969); Canadian Journal of Biochemistry, 47, 547–552 (1969); The Journal of Immunology, 93, 629–640 (1964); The Journal of Immunology, 104, 279–288 (1970); The Journal of Immunology, 106, 241–245 (1971); and The Journal of Immunology, 111, 1061–1066 (1973).

It has been reported that the known complement inhibitors epsilon-aminocaproic acid, Suramin and tranexamic acid all have been used with success in the treatment of hereditary angioneurotic edema, a disease state resulting from an inherited deficiency or lack of function of the serum inhibitor of the activated first component of complement (C1 inhibitor), The New England Journal of Medicine, 286, 808–812 (1972).

The compounds of the present invention may be administered internally, e.g., orally, intra-articularly or parenterally, e.g., intra-articular, to a warm-blooded animal to inhibit complement in the body fluid of the animal, such inhibition being useful in the amelioration or prevention of those reactions dependent upon the function of complement, such as inflammatory process and cell membrane damage induced by antigen-antibody complexes. A range of doses may be employed depending on the mode of administration, the condition being treated and the particular compound being used. For example, for intravenous or subcutaneous use from about 5 to about 50 mg/kg/day, or every six hours for more rapidly excreted salts, may be used. For intra-articular use for large joints such as the knee, from about 2 to about 20 mg/joint per week may be used, with proportionally smaller doses for smaller joints. The dosage range is to be adjusted to provide optimum therapeutic response in the warm-blooded animal being treated. In general, the amount of compound administered can vary over a wide range to provide from about 5 mg/kg to about 100 mg/kg of body weight of animal per day. The usual daily dosage for a 70 kg subject may vary from about 350 mg to about 3.5 g. Unit doses of the acid or salt can contain from about 0.5 mg to about 500 mg.

While in general the sodium salts of the acids of the invention are suitable for parenteral use, other salts may also be prepared, such as those of primary amines, e.g., ethylamine; secondary amines, e.g., diethylamine or diethanol amine; tertiary amines, e.g., pyridine or triethylamine or 2-dimethylaminomethyl-dibenzofuran; aliphatic diamines, e.g., decamethylenediamine; and aromatic diamines, can be prepared. Some of these are soluble in water, others are soluble in saline solution, and still others are insoluble and can be used for purposes of preparing suspensions for injection. Furthermore as well as the sodium salt, those of the alkali metals, such as potassium and lithium; of ammonia; and of the alkaline earth metals, such as calcium or magnesium, may be employed. It will be apparent, therefore, that these salts embrace, in general derivatives of salt-forming cations.

In therapeutic use, the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as nontoxic pharmaceutically acceptable diluents or carriers.

The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate non-toxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term dosage form, as described herein, refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement inhibiting activity of the compounds of this invention has been demonstrated by one or more of the following identified tests: (i) Test, Code 026 (C1 inhibitor) - This test measures the ability of activated human C1 to destroy fluid phase human C2 in the presence of C4 and appropriate dilutions of the test compound. An active inhibitor protects C2 and C1 and C4; (ii) Test, Code 035 (C3-C9 inhibitor) - This test determines the ability of the late components of human complement (C3-C9) to lyse EAC 142 in the presence of appropriate dilutions of the test compound. An active inhibitor protects EAC 142 from lysis by human C3-C9; (iii) Test, Code 036 (C-Shunt inhibitor) - In this test human erythrocytes rendered fragile are lysed in autologous serum via the shunt pathway activated by cobra venom factor in the presence of appropriate dilutions of the test compound. Inhibition of the shunt pathway results in failure of lysis; (iv) Forssman Vasculitis Test - Here, the well known complement dependent lesion, Forssman vasculitis, is produced in guinea pigs by intradermal injection of rabbit anti-Forssman antiserum. The lesion is measured in terms of diameter, edema and hemorrhage and the extent to which a combined index of these is inhibited by prior intraperitoneal injection of the test compound at 200 mg/k is then reported, unless otherwise stated; (v) Forssman Shock Test - Lethal shock is produced in guinea pigs by an i.v. injection of anti-Forssman antiserum and the harmonic mean death time of treated guinea pigs is compared with that of simultaneous controls; (vi) Complement Level Reduction Test - In this test, the above dosed guinea pigs, or others, are bled for serum and the complement level is determined in undiluted serum by the capillary tube method of U.S. Pat. No. 3,876,376 and compared to undosed control guinea pigs; and (vii) Cap 50 Test - Here, appropriate amounts of the test compound are added to a pool of guinea pig serum in vitro, after which the undiluted serum capillary tube assay referred to above is run. The concentration of compound inhibiting 50% is reported.

With reference to Table I, guinea pigs weighing about 300 g were dosed intravenously (i.v.) or intraperitoneally (i.p.) with 200 mg/kg of the test compound dissolved in saline and adjusted to ph 7-8. One hour after dosing, the guinea pigs were decapitated, blood was collected and the serum separated. The serum was tested for whole complement using the capillary tube assay. Percent inhibition was calculated by comparison with simultaneous controls. The results appear in Table I together with results of tests, code 026, 035, 036, Cap 50, % inhibition and Forssman shock. Table I shows that the compounds of the invention possess highly significant in vitro and in vivo, complement inhibiting activity in warm-blooded animals.

TABLE I
Biological Activities

| Compound | C1 026* Wells | C-Late 035* Wells | Shunt Inhibition 036* Wells | Cap 50* | In Vivo Activity (Guinea Pig) % Inhibition Intraperitoneal Time (minutes) 30 | 60 | 120 |
|---|---|---|---|---|---|---|---|
| 5,5′,5″-[1,3,6-Naphthalenetriyltris-(sulfonylimino)]tris[2-hydroxyisophthalic acid] | +5** | +1 | +4 | 29 | −69 | −59 | −58 |
| 5,5′,5″-[1,3,6-Naphthalenetriyltris-(sulfonylimino)]triisophthalic acid hexasodium salt | +4 +6 | N N | N +2 | 5 | −67 | −79 | −84 |
| 3,3′,3″-[1,3,6-Naphthalenetriyltris-(sulfonylimino)]tris[6-hydroxy benzoic acid) | +1 | N | N | | | | |
| 4,4′,4″-[1,3,6-Naphthalenetriyltris-(sulfonylimino)]tribenzoic acid trisodium salt | +3 +4 | N N | N N | 411 | | | |
| 5,5′,5″-[1,3,6-Naphthalenetriyltris-(sulfonylimino)]tri-1,2,3-benzenetri- | +8 +8 | +1 N | +4 +5 | 43 | −63 | −71 | −71 |

TABLE I-continued

Biological Activities

| Compound | Cl 026* Wells | C-Late 035* Wells | Shunt Inhibition 036* Wells | Cap 50* | In Vivo Activity (Guinea Pig) % Inhibition Intraperitoneal Time (minutes) 30 | 60 | 120 |
|---|---|---|---|---|---|---|---|
| carboxylic acid nonasodium salt 3,3',3"-[1,3,6-Naphthalenetriyltris-(sulfonylimino)]tribenzoic acid | +3 | N | N | ≧500 | | | |
| 5,5',5"-[1,3,6-Naphthalenetriyltris-(sulfonylimino)]triisophthalic acid | +6 | N | +2 | 22 | −84 | −88 | −96 |
| 5,5',5"-[1,3,6-Naphthalenetriyltris-(sulfonylimino)]triisophthalic acid hexasodium salt | +3 | N | N | ≧500 | | | |

*Code designation for tests employed as referred herein.
**Activity in wells a serial dilution assay. Higher well number indicates higher activity.
The serial dilutions are two-fold.
N=Negative

EXAMPLE 1

5,5',5"-[1,3,6-Naphthalenetriyltris(sulfonylimino)]-tris[2-hydroxyisophthalic acid]hexamethyl ester

To a mixture of 40 ml of concentrated sulfuric acid and 33 ml of concentrated nitric acid stirred for 10 minutes is slowly added 10 ml of glacial acetic acid and a suspension of 10 g of 2-hydroxyisophthalic acid (prepared as described in Organic Synthesis Coll., Vol. V, 617) in 20 ml of glacial acetic acid. The reaction mixture is cooled and an additional 10 ml of acetic acid is added. The solid formed is dissolved in water, and is extracted with diethyl ether. The ether extract is washed with saturated sodium chloride, dried over anhydrous sodium sulfate and evaporated to an orange oil identified as 2-hydroxy-5-nitroisophthalic acid.

The product is treated with 250 ml of methyl alcohol and 10 ml of concentrated sulfuric acid, and is refluxed for 5 days. The reaction mixture is cooled and concentrated in vacuo to afford a solid. The solid is collected by filtration, washed with water, followed by ether, then is air dried. The material is recrystallized from ethyl acetate-hexane to afford 2.84 g of 2-hydroxy-5-nitroisophthalic acid dimethyl ester.

A 2.0 g portion of the preceding compound and 200 mg of 10% palladium on carbon catalyst in 200 ml of ethyl acetate is hydrogenated on a Parr shaker until no additional hydrogen is absorbed. The reaction mixture is then filtered through diatomaceous earth. The filtrate is evaporated to afford a yellow solid. The solid is recrystallized from ethyl acetate-hexane to yield 1.04 g of 2-hydroxy-5-aminoisophthalic acid dimethyl ester.

A mixture of 60.0 g of 1,3,6-naphthalenetrisulfonic acid trisodium salt, 250 ml of thionyl chloride and 5 drops of dimethylformamide is refluxed for 16 hours. The solid is removed by filtration and the filtrate is evaporated. The residue is triturated with chloroform, and filtered, washed with chloroform, and dried to yield 25.4 g of 1,3,6-naphthalenetrisulfonyl chloride as a white solid.

To a stirred solution of 695 mg of 2-hydroxy-5-aminoisophthalic acid dimethyl ester, 10 ml of acetonitrile and 270 mg of pyridine is added 428 mg of 1,3,6-naphthalenetrisulfonyl chloride. The reaction mixture is stirred for 16 hours under an atmosphere of argon, then is acidified with dilute hydrochloric acid, and the acetonitrile is removed by distillation in vacuo. The aqueous mixture is extracted twice with ether. The ether extract is evaporated to yield a brown oil which affords brown crystals on being worked with ether. The crystals are collected, washed with ether, and dried in vacuo to give 780 mg of 5,5',5"-[1,3,6-naphthalenetriyltris(sulfonylimino)]tris[2-hydroxyisophthalic acid]hexamethyl ester as a tan powder.

EXAMPLE 2

5,5',5"-[1,3,6-Naphthalenetriyltris(sulfonylimino]-tris[2-hydroxyisophthalic acid]

A solution of 680 mg of the product of Example 1 in 10 ml of 1N sodium hydroxide is stirred for 5 hours, then is acidified with dilute hydrochloric acid to afford a brown gum. The gum is separated and washed twice with both water and ethanol, then once with ether affording a light brown powder. The filtrate above is evaporated and the resulting residue is washed several times with water, then ether, affording a brown crystalline powder. The fractions are combined, recrystallized from ethanol, and dried in vacuo to yield 428 mg of the product of the Example as orange-brown crystals.

EXAMPLE 3

5,5',5"-[1,3,6-Naphthalenetriyltris(sulfonylimino)]-triisophthalic acid hexakis(2-methoxyethyl)ester

A mixture of 500 g of 5-nitroisophthalic acid, 3500 g of thionyl chloride and 6.0 ml of dimethylformamide is heated gradually until the evolution of gases subsides. Heating is continued for approximately 2 hours with stirring until solution is achieved, then reflux is continued for an additional 30 minutes. The resulting clear solution is allowed to stand, then is evaporated in vacuo to afford an oil. The oil solidifies and is recrystallized twice from carbon tetrachloride to give 501 g of 5-nitroisophthaloyl chloride.

A mixture of 100 g of the product above and 100 g of 2-methoxyethanol (dried over molecular sieves) in 400 ml of acetonitrile (dried over molecular sieves) is heated to reflux on a steam bath. Heating is continued for 15 minutes, then the mixture is cooled to room temperature and poured into 2 liters of cold water with vigorous stirring. The product is collected by filtration and air dried to give 129 g of material. Additional product (5.7 g) is recovered from the filtrate by extraction with benzene. The combined fractions are dissolved in 580 ml of hot ethyl alcohol. The solution is neutralized with 5.0 ml of 5N sodium hydroxide, then diluted with 450 ml of water. The solution is kept at room temperature, crystals separate, and then the mixture is placed overnight in a chill room (5° C.). The colorless needles are recrystallized from a solution of 450 ml of ethanol and 350 ml of water to give 92.1 g of 5-nitroisophthalic acid bis(2-methoxyethyl)ester.

A total of 86.0 g of the preceding product is hydrogenated on a Parr shaker in 300 ml of ethyl acetate using 2.0 g of 10% palladium on carbon catalyst. The mixture is filtered and the filtrate evaporated to give off-white crystals. The crystals are dissolved in 350 ml of hot benzene and diluted with 140 ml of hexane. The solution is allowed to crystallize overnight at room temperature to yield 72.0 g of 5-aminoisophthalic acid bis(2-methoxyethyl)ester.

To a solution of 15.16 g of the product above and 6.18 g of dimethylaniline in 75 ml of acetonitrile is added 7.2 g of 1,3,6-naphthalenetrisulfonyl chloride. The solution is refluxed on a steam bath for 2 hours, then is poured into 250 ml of cold water and stirred until a product is solidified. The product is collected and washed with water, then is dissolved in 150 ml of methylene chloride:methanol (2:1) and the solution is dried over anhydrous sodium sulfate. Evaporation in vacuo provides a solid which is dissolved in 100 ml of methylene chloride. The solution is dried over sodium sulfate for 16 hours filtered and is concentrated on a steam bath with the addition of methanol until 2/3 of the methylene chloride has been removed, at which point a thick colorless paste is formed. The mixture is diluted to 250 ml with methanol and filtered. The product is washed on the filter with methanol and ether and air dried for 16 hours. The material is dissolved in 500 ml of refluxing acetonitrile, filtered and allowed to crystallize 16 hours. The product is filtered and dried to give 16.35 g of 5,5',5''-[1,3,6-naphthalenetriyltris(sulfonylimino)]-triisophthalic acid hexakis(2-methoxyethyl)ester as a colorless powder.

EXAMPLE 4

5,5',5''-[1,3,6-Naphthalenetriyltris(sulfonylimino)]-triisophthalic acid hexasodium salt A mixture of 9.05 g of the product of Example 3 and 45 ml of 2N sodium hydroxide is stirred at room temperature for 45 minutes. The solution is filtered, the filtrate is neutralized with 2.5 ml of glacial acetic acid, and diluted with 250 ml of ethanol. The product formed is collected by filtration, washed with ethanol followed by ether and dried to give 7.85 g of the product of the Example as a yellow powder.

EXAMPLE 5

3,3',3''-[1,3,6-Naphthalenetriyltris(sulfonylimino)]tris[6-hydroxybenzoic acid]trimethyl ester A solution of 20.0 g of 5-aminosalicylic acid, 250 ml of methanol and 10 ml of concentrated sulfuric acid is refluxed overnight. The reaction mixture is cooled, made alkaline with dilute aqueous sodium carbonate solution and concentrated. The resulting solid is separated and washed with water. The solid is then washed with ether, and the ether is evaporated to dryness yielding a brown solid. The aqueous filtrate above is extracted with ether, the extract is dried over anhydrous sodium sulfate, and evaporated yielding a brown solid. The solids are combined and recrystallized from ether to afford 10.7 g of 5-aminosalicylic acid methyl ester.

To a stirred solution of 2.1 g of the above compound, 994 mg of pyridine and 10 ml of acetonitrile is added 1.7 g of 1,3,6-naphthalenetrisulfonyl chloride. The mixture is stirred for 16 hours, then acidified with dilute hydrochloric acid, concentrated and extracted with ether. The extract is washed with saturated sodium chloride, dried over anhydrous sodium sulfate and evaporated to give 2.91 g of the product of the Example as a pink solid.

EXAMPLE 6

3,3',3''-[1,3,6-Naphthalenetriyltris(sulfonylimino)]tris[6-hydroxybenzoic acid]

A solution of 1.5 g of the product of Example 5 in 25.0 ml of 1N sodium hydroxide is stirred at room temperature for 48 hours. The solution is acidified with dilute hydrochloric acid. The resulting solid is separated, washed with water and dried to give 920 mg of the product of the Example as a brown powder.

EXAMPLE 7

4,4',4''-[1,3,6-Naphthalenetriyltris(sulfonylimino)]-tribenzoic acid trimethyl ester To a warmed and stirred mixture of 10.7 g of p-aminobenzoate, 200 ml of acetonitrile and 5.59 g of pyridine is added 10.0 g of 1,3,6-naphthalenetrisulfonyl chloride. The mixture is stirred and refluxed for 16 hours, then is cooled and filtered. The filtrate is poured into cold water with the separation of a solid after stirring and standing at room temperature. The solid is separated, washed with water, dissolved in 60 ml of 30% acetone in benzene and filtered through hydrous magnesium silicate. The latter containing the product is washed with 30% acetone in benzene, then is treated with acetone to dissolve the product. The acetone eluates are combined and evaporated to yield a residue which is dissolved in 200 ml of acetonitrile and allowed to stand 16 hours in a chill room (5° C.). The white solid formed is separated, washed with acetonitrile and petroleum ether, and dried at 70° C. to give 12.0 g of 4,4',4''-[1,3,6-naphthalenetriyltris(sulfonylimino)]tribenzoic acid trimethyl ester.

EXAMPLE 8

4,4',4''-[1,3,6-Naphthalenetriyltris(sulfonylimino)]-tribenzoic acid trisodium salt A 9.0 g portion of the product of Example 7 is dissolved in 46.5 ml of 2N sodium hydroxide and stirred for 45 minutes. The solution is neutralized with 2.7 ml of glacial acetic acid and diluted with 200 ml of ethanol. A yellow solid separates which is collected by filtration, washed with ethanol and ether, and dried to give 8.7 g of the product of the Example.

EXAMPLE 9

5,5',5''-[1,3,6-Naphthalenetriyltris(sulfonylimino)]tri-1,2,3-benzenetricarboxylic acid nonaphenyl ester To a stirred mixture of 125 g of 1,2,3-benzenetricarboxylic acid and 900 ml of concentrated sulfuric acid at 60°–70° C. is added, gradually over a 2 hour period, 312 g of potassium nitrate. The mixture is heated at 135°–140° C. for 16 hours, cooled and treated with ice and water. Some solid is separated out and is dissolved in water. The entire aqueous mixture is extracted with ether, the extract is washed with water and dried over magnesium sulfate. The ether is concentrated to a small volume, and petroleum ether is added to precipitate a white solid. The solid is collected and dried to give 76.5 g of 5-nitro-1,2,3-benzenetricarboxylic acid.

A mixture of 50.0 g of the preceding product, 300 ml of thionyl chloride and 2.0 ml of dimethylformamide is heated under reflux for 16 hours. The solvent is evaporated in vacuo and the residue is dissolved in chloroform. The chloroform is concentrated to a small volume, and the residue is dissolved in carbon tetrachloride. On standing, a yellow solid is separated, collected and dried to give 30.0 g of material. A mixture of this material with 100 ml of thionyl chloride and 2.0 ml of dimethylformamide is refluxed for 16 hours. The solvent is evaporated and the resulting yellow solid is crystallized from chloroform:carbontetrachloride to give 23.0 g of 5-nitro-1,2,3-benzenetricarbonyl chloride.

To a stirred solution of 30.6 g of phenol in 100 ml of pyridine (dried over molecular sieves) is added 22.7 g of the product above. The solution is heated on a steam bath for one hour, cooled and poured into 500 ml of cold water with vigorous stirring resulting in the separation of a solid. The mixture is filtered, and the solid is washed with water to give a brown powder. The product is dissolved in 100 ml of methylene chloride and filtered. The filtrate is boiled on a steam bath and 250 ml of ethanol is added portionwise to the boiling solution until all of the methylene chloride has been removed. The mixture is cooled to room temperature, and the product formed is separated, washed with ethanol and ether, then is dissolved in 75.0 ml of methylene chloride. It is then recrystallized from 200 ml of ethanol as above, separated and dried to yield 30.8 g of 5-nitro-1,2,3-benzenetricarboxylic acid triphenyl ester.

A solution of 29.0 g of the above nitrocompound in dimethylformamide is hydrogenated on a Parr shaker in the presence of 10% palladium-on-carbon catalyst. The mixture is filtered through diatomaceous earth and the filtrate is diluted with water and extracted with methylene chloride. The extract is dried over anhydrous sodium sulfate and evaporated to give an oil. The oil is crystallized from ether, and the product is recrystallized from benzene and twice from ethanol to provide 15.0 g of 5-amino-1,2,3-benzenetricarboxylic acid triphenyl ester as tan crystals.

To a stirred solution of 13.6 g of the preceding product in 50 ml of pyridine (dried over 4A molecular sieves) is added 4.24 g of 1,3,6-naphthalenetrisulfonyl chloride. The mixture is stirred for 10 minutes, then is heated on the steam bath for 30 minutes, cooled and poured into 300 ml of ice-cold 2.05N hydrochloric acid. The mixture is stirred until the product solidifies. The material is collected by filtration and washed with water until neutral, and dried to give 19.3 g of crude product. The crude product is treated by conventional chromatographic techniques to obtain a fraction of 14.9 g of material. This material is recrystallized twice from methylene chloride:ether (2:3), and dried by conventional means to give 9.8 g of the product of the Example as colorless crystals.

EXAMPLE 10

5,5',5''-[1,3,6-Naphthalenetriyltris(sulfonylimino)]-tri-1,2,3-benzenetricarboxylic acid nonasodium salt A 6.7 g portion of the product of Example 9 is added to 50 ml of 2N sodium hydroxide and stirred for 30 minutes, then 3.68 ml of glacial acetic acid is added. The solution is poured with vigorous stirring into 500 ml of absolute ethanol. The fine granular precipitate produced is separated by filtration and is washed with ethanol and ether, then is dissolved in 35.0 ml of water containing 1.0 g of sodium acetate trihydrate. The solution is filtered through diatomaceous earth and poured into 350 ml of absolute ethanol. The product of the Example is separated and dried to give 5.3 g of yellow powder.

EXAMPLE 11

3,3',3''-[1,3,6-Naphthalenetriyltris(sulfonylimino)]-tribenzoic acid trimethyl ester To a stirred mixture of 10.7 g of methyl-m-aminobenzoate, 80 ml of acetonitrile and 6.1 ml of pyridine is added 10.8 g of 1,3,6-naphthalenetrisulfonyl chloride. The mixture is stirred and refluxed for 2 hours, then is cooled. The solution is poured into water resulting in the separation of an oil which solidifies on standing and on being stirred. The separated solid is dried, dissolved in acetonitrile and filtered. The solvent is evaporated in vacuo, and the residue is dried to give 16.0 g of the product of the Example as a beige solid.

EXAMPLE 12

3,3',3''-[1,3,6-Naphthalenetriyltris(sulfonylimino)]-tribenzoic acid trisodium salt A mixture of 12.0 g of the product of Example 11 and 62.0 ml of 2N sodium hydroxide is stirred for 45 minutes. The solution is neutralized with 3.6 ml of glacial acetic acid and diluted with 400 ml of ethanol. The solvent is concentrated in vacuo to a small volume. Then it is diluted again with ethanol with the separation of an oil. The solvent is decanted off, and the oil is triturated with fresh ethanol to produce a yellow solid. The solid is separated, washed with ethanol and ether, and dried at 70° C. to yield 7.3 g of the product of the Example.

EXAMPLE 13

5,5',5''-[1,3,6-Naphthalenetriyltris(sulfonylimino)]-triisophthalic acid

A mixture of 12.06 g of the product of Example 3 and 60 ml of 2N sodium hydroxide is stirred for one hour. The resulting yellow solution is acidified with 65 ml of 2N hydrochloric acid to give a colorless gum which solidifies on standing. The mixture is filtered and the separated product is washed with water until the washings are neutral. The material is dried in vacuo, then is pulverized, and dried again to give 8.36 g of the product of the Example as a colorless powder.

EXAMPLE 14

5,5',5''-[1,3,6-Naphthalenetriyltris(sulfonylmethylimino)]triisophthalic acid hexakis(2-methoxyethyl)ester To a stirred solution of 6.03 g of the product of Example 3 in 25 ml of dimethylformamide, which is cooled in a water-bath, is added dropwise 3.25 ml of 5N sodium hydroxide followed by 3.75 ml of methyl iodide. The mixture is stirred in a stoppered flask for a total of 3 hours at room temperature. The mixture is filtered, and the separated product is washed on the filter with a small amount of dimethylformamide Then it is stirred in 100 ml water, separated and dried. The product is dissolved in 30 ml of methylene chloride and filtered through diatomaceous earth. The filtrate is boiled wit the addition of methanol until all the methylene chloride is removed. The mixture is allowed to cool and crystallize. The product is collected and dried to give 5.7 g of colorless crystals as the product of the Example.

EXAMPLE 15

5,5′,5″-[1,3,6-Naphthalenetriyltris(sulfonylmethylimino)]triisophthalic acid hexasodium salt To a stirred, warm solution of 5.0 g of the product of Example 14 in 40 ml of dioxane is added 20 ml of 2N sodium hydroxide. The mixture is stirred vigorously for 10 minutes, then 10 ml of water is added, and stirring is continued for a total of 1 hour. The resulting solution is poured into 300 ml of absolute ethanol. The mixture is filtered and the separated product is washed with ethanol and ether. The product with 1.0 g of sodium acetate trihydrate is dissolved in 20 ml of water and poured into 250 ml of absolute ethanol. The resulting mixture is stirred for one hour, and then is filtered. The separated product is washed with ethanol and ether, and dried to give 4.22 g of the product of the Example as a beige powder.

EXAMPLE 16

Preparation of Compressed Table

| Ingredient | mg/Tablet |
|---|---|
| Active Compound | 0.5–500 |
| Dibasic Calcium Phosphate N.F. | qs |
| Starch USP | 40 |
| Modified Starch | 10 |
| Magnesium Stearate USP | 1–5 |

EXAMPLE 17

Preparation of Compressed Table - Sustained Action

| Ingredient | mg/Tablet |
|---|---|
| Active Compound as Aluminum Lake*, Micronized | 0.5–500(as acid equivalent) |
| Dibasic Calcium Phosphate N.F. | qs |
| Alginic Acid | 20 |
| Starch USP | 35 |
| Magnesium Stearate USP | 1–10 |

*Complement inhibitor plus aluminum sulfate yields aluminum complement inhibitor. Complement inhibitor content in aluminum lake ranges from 5–30%.

EXAMPLE 18

Preparation of Hard Shell Capsule

| Ingredient | mg/Capsule |
|---|---|
| Active Compound | 0.5–500 |
| Lactose, Spray Dried | qs |
| Magnesium Stearate | 1–10 |

EXAMPLE 19

Prepartion of Oral Liquid (Syrup)

| Ingredient | % W/V |
|---|---|
| Active Compound | 0.05–5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 20

Preparation of Oral Liquid (Elixir)

| Ingredient | % W/V |
|---|---|
| Active Compound | 0.05–5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 21

Preparation of Oral Suspension (Syrup)

| Ingredient | % W/V |
|---|---|
| Active Compound as Aluminum Lake, Micronized | 0.05–5 (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 22

Preparation of Injectable Solution

| Ingredient | % W/V |
|---|---|
| Active Compound | 0.05–5 |
| Benzyl Alcohol N.F. | 0.9 |
| Water for Injection | 100.0 |

EXAMPLE 23

Preparation of Injectable Oil

| Ingredient | % W/V |
|---|---|
| Active Compound | 0.05–5 |
| Benzyl Alcohol | 1.5 |
| Sesame Oil qs ad | 100.0 |

EXAMPLE 24

Preparation of Intra-Articular Product

| Ingredient | Amount |
|---|---|
| Active Compound | 2–20 mg |
| NaCl (physiological saline) | 0.9% |
| Benzyl Alcohol | 0.9% |
| Sodium Carboxymethylcellulose | 1–5% |
| pH adjusted to 5.0–7.5 | |
| Water for Injection qs ad | 100% |

EXAMPLE 25

Preparation of Injectable Depo Suspension

| Ingredient | % W/V |
|---|---|
| Active Compound | 0.05–5 (acid equivalent) |
| Polysorbate 80 USP | 0.2 |
| Polyethylene Glycol 4000 USP | 3.0 |
| Sodium Chloride USP | 0.8 |
| Benzyl Alcohol N.F. | 0.9 |
| HCl to pH 6-8 | qs |
| Water for Injection qs ad | 100.0 |

We claim:

1. A method of inhibiting the complement system in a body fluid which comprises subjecting said body fluid to the action of an effective complement inhibiting amount of a compound of the formula:

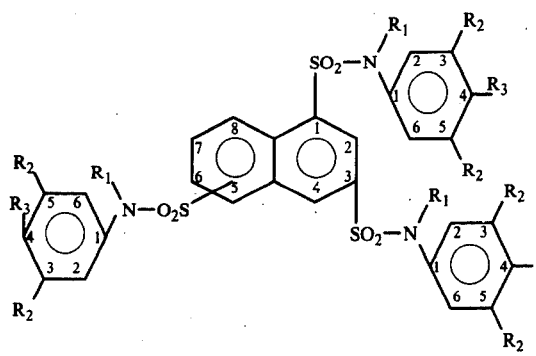

wherein $R_1$ is selected from the group consisting of hydrogen and methyl; $R_2$ is selected from the group consisting of hydrogen, carboxyl and $COOR_4$, wherein $R_4$ is selected from the group consisting of alkali metal and alkaline earth metal; $R_3$ is selected from the group consisting of hydrogen, hydroxy and $COOR_4$, wherein $R_4$ is as previously defined; with the proviso that each phenyl must contain at least one $COOR_4$; and the nontoxic pharmaceutically acceptable salts thereof.

2. A method according to claim 1, wherein said body fluid is blood serum.

3. A method according to claim 1, wherein said compound is 5,5',5''-[1,3,6-naphthalenetriyltris(sulfonylimino)]tris[2-hydroxyisophthalic acid].

4. A method according to claim 1, wherein said compound is 5,5',5''-[1,3,6-naphthalenetriyltris(sulfonylimino)]-triisophthalic acid hexasodium salt.

5. A method according to claim 1, wherein said compound is 3,3',3''-[1,3,6-naphthalenetriyltris(sulfonylimino)]tris[6-hydroxybenzoic acid].

6. A method according to claim 1, wherein said compound is 4,4',4''-[1,3,6-naphthalenetriyltris(sulfonylimino)]tribenzoic acid trisodium salt.

7. A method according to claim 1, wherein said compound is 5,5',5''-[1,3,6-naphthalenetriyltris(sulfonylimino)]tri-1,2,3-benzenetricarboxylic acid nonasodium salt.

8. A method according to claim 1, wherein said compound is 3,3',3''-[1,3,6-naphthalenetriyltris(sulfonylimino)]tribenzoic acid trisodium salt.

9. A method according to claim 1, wherein said compound is 5,5',5''-[1,3,6-naphthalenetriyltris(sulfonylimino)]triisophthalic acid.

10. A method according to claim 1, wherein said compound is 5,5',5''-[1,3,6-naphthalenetriyltris(sulfonylimino)]triisophthalic acid hexasodium salt.

11. A method of inhibiting the complement system in a warm-blooded animal which comprises internally administering to said animal an effective complement inhibiting amount of a compound of the formula:

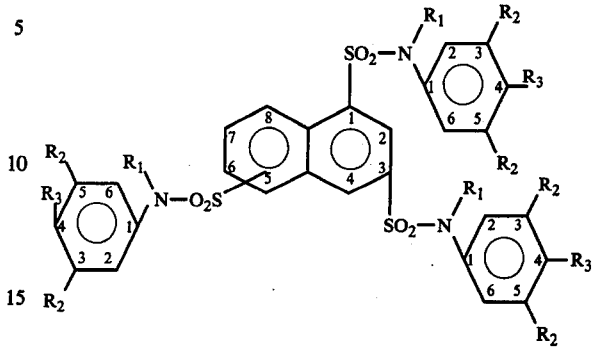

wherein $R_1$ is selected from the group consisting of hydrogen and methyl; $R_2$ is selected from the group consisting of hydrogen, carboxyl and $COOR_4$, wherein $R_4$ is selected from the group consisting of alkali metal and alkaline earth metal; $R_3$ is selected from the group consisting of hydrogen, hydroxy and $COOR_4$, wherein $R_4$ is as previously defined; with the proviso that each phenyl must contain at least one $COOR_4$; and the nontoxic pharmaceutically acceptable salts thereof.

12. A method according to claim 11, wherein said compound is administered intra-articularly.

13. A method according to claim 11, wherein said compound is 5,5',5''-[1,3,6-naphthalenetriyltris(sulfonylimino)] tris[2-hydroxyisophthalic acid].

14. A method according to claim 11, wherein said compound is 5,5',5''-[1,3,6-naphthalenetriyltris(sulfonylimino)]triisophthalic acid hexasodium salt.

15. A method according to claim 11, wherein said compound is 3,3',3''-[1,3,6-naphthalenetriyltris(sulfonylimino)]tris[6-hydroxybenzoic acid].

16. A method according to claim 11, wherein said compound is 4,4',4''-[1,3,6-naphthalenetriyltris(sulfonylimino)]tribenzoic acid trisodium salt.

17. A method according to claim 11, wherein said compound is 5,5',5''-[1,3,6-naphthalenetriyltris(sulfonylimino)]-tri-1,2,3-benzenetricarboxylic acid nonasodium salt.

18. A method according to claim 11, wherein said compound is 5,5',5''-[1,3,6-naphthalenetriyltris(sulfonylimino)]-tribenzoic acid trisodium salt.

19. A method according to claim 11, wherein said compound is 5,5',5''-[1,3,6-naphthalenetriyltris(sulfonylimino)]-triisophthalic acid.

20. A method according to claim 11, wherein said compound is 5,5',5''-[1,3,6-naphthalenetriyltris(sulfonylimino)]-triisophthalic acid hexasodium salt.

* * * * *